United States Patent [19]

Ledley

[11] 4,409,616
[45] Oct. 11, 1983

[54] DIGITAL DENTAL SYSTEM AND METHOD

[75] Inventor: Robert S. Ledley, Silver Spring, Md.

[73] Assignee: Georgetown University, Washington, D.C.

[21] Appl. No.: 245,997

[22] Filed: Mar. 20, 1981

[51] Int. Cl.³ .......................... H04N 7/18; H04N 5/32
[52] U.S. Cl. ...................................... 358/111; 378/99; 378/38; 378/40
[58] Field of Search .................. 358/93, 83, 111, 112, 358/113, 106; 378/98, 99, 100, 176, 29, 38, 40, 62, 63, 165, 166

[56] References Cited

U.S. PATENT DOCUMENTS

| | | | |
|---|---|---|---|
| 3,743,832 | 7/1973 | Wright | 250/61.5 |
| 3,849,596 | 11/1974 | Lawrence | 358/93 |
| 4,012,638 | 3/1977 | Altschuler et al. | 250/491 |
| 4,100,417 | 7/1978 | Goetzl et al. | 250/505 |
| 4,158,138 | 6/1979 | Hellstrom | 250/402 |
| 4,188,537 | 2/1980 | Franke | 250/416 |
| 4,210,812 | 7/1980 | Ando et al. | 358/111 |
| 4,229,797 | 10/1980 | Ledley | 250/515 |
| 4,239,971 | 12/1980 | Cushman | 250/439 |
| 4,262,306 | 4/1981 | Renner | 358/111 |

OTHER PUBLICATIONS

Frost et al., "A Digital Video Acquisition System for Extraction of Subvisual Information in Diagnostic Medical Imaging," SPIE vol. 127, Optical Instrumentation in Medicine 9/77.

*Primary Examiner*—Jin F. Ng
*Assistant Examiner*—Edward L. Coles
*Attorney, Agent, or Firm*—Oblon, Fisher, Spivak, McClelland & Maier

[57] ABSTRACT

A digital dental system and method for real time display of a patient's dental image to detect changes with respect to at least one previous dental image of the patient. The system comprises an imaging unit for obtaining a real time dental image from the patient, a converter for converting the real time dental image to digital form, an input device for inputting further digital signals corresponding to at least one previous dental image of the patient, a processor for processing the digital signals and the further digital signals to develop corresponding display signals and further display signals, and a display unit and at least one further display unit for simultaneously and in real time displaying the dental image and the at least one previous dental image, respectively, of the patient. A preferred embodiment of the invention involves whole picture processing of the present and previous dental images to determine changes or differences therebetween. Further features of the present invention include the provision of an alignment motion controller for aligning an image intensifier and an X-ray tube (forming the imaging unit), as well as the provision of a capability for selective display, on one of the display units, of either the current X-ray image or a previously obtained (and stored) X-ray image.

8 Claims, 2 Drawing Figures

DIGITAL DENTAL SYSTEM AND METHOD

BACKGROUND OF THE INVENTION

1. Field of the Invention

The present invention relates to a digital dental system and method, and more particularly to a method and system for the real-time display of a patient's dental image to detect changes with respect to at least one previous dental image of the patient.

2. Description of the Prior Art

Dental systems and techniques have yet to exploit fully sophisticated technology, and, as a result, much inefficiency and slowness of operation still characterizes dental treatment afforded to patients.

For example, typically, a dental patient visits a dental clinic or the office of a dentist, and an x-ray is taken. It is then necessary for the x-ray to be developed, and then analyzed by the dentist in order to determine the patient's dental condition. At the completion of the visit, or at the completion of treatment, the X-ray is manually stored in the dental files for future use.

On a subsequent visit (for example, after a six-month or one-year period has passed), a further X-ray is taken in order to determine the patient's dental condition. This X-ray must also be developed and then analyzed by the dentist. It is typical for the dentist, under such circumstances of a repeat visit, to compare the present X-ray with the previous X-ray(s), in order to determine whether any change in the patient's dental condition has taken place in the intervening period since the last visit. In making such a comparison, the dentist makes a human (visual) judgment as to differences in the patient's dental condition between the previous and present X-rays.

The technique described above has several disadvantages: (1) it is necessary for X-rays to be stored manually in the dental files of the clinic or dentist, and thus possible loss or misplacement of the X-ray becomes more probable; (2) each time an X-ray is taken, it is necessary for the X-ray to be developed, and this results in much time lost by the dentist, a substantial amount of expense experienced by the dentist (and thus, experienced by the patient), and a substantial amount of time spent by the patient at the dental clinic or office (waiting for the X-ray to be developed); (3) each time the patient visits the dentist or dental clinic, it is necessary for the previous X-rays to be taken from the files, utilized during the treatment, and then replaced (hopefully properly replaced) in the files, and this increases the probability of loss or misfiling of X-rays; and (4) finally, since the dentist must make a human/visual judgment in determining whether changes in the dental condition of the patient have taken place since the last visit, the possibility of error or oversight exists, and, in any event, much time is consumed (wasted) in the examination/comparison of previous and present X-rays.

With the advent of data processing and automation, computers have found usefulness in the storage and display of dental X-rays. For example, U.S. Pat. No. 4,188,537—Franke discloses a dental apparatus for X-ray diagnosis, the apparatus having an X-ray tube and a carrier for a radiation receiver disposed on a unit for rotation about a support for holding the head of the patient, the apparatus being further characterized by the inclusion, in the radiation receiver, of a transducer means for forming electrical signals corresponding to a measured radiation intensity. The apparatus is further provided with a data processing installation having means for storing the measured radiation intensity for one exposure sequence, and means for creating a survey image from the stored information and displaying the image on a display device.

A further system is disclosed in U.S. Pat. No. 4,210,812—Ando et al., the system including an X-ray imaging diagnostic apparatus emitting a low X-ray radiation dose. The apparatus is disclosed as comprising an X-ray generating source, an optical system having a fluorescent screen for receiving the X-ray image at an aperture portion thereof, a high-sensitivity imaging device, a control unit, an image storing memory circuit for storing an image signal from the control unit, and a monitor circuit for displaying the image signal.

A further system, disclosed in U.S. Pat. No. 4,158,138—Hellstrom, consists of a diagnostic X-ray system which is operative, in response to control signals from a stored program digital computer, to generate an X-ray beam and to produce an image of the object through which the X-ray beam passes. That is to say, computer-controlled X-ray generation is provided in such an arrangement.

Finally, prior art technology relating to dental systems as also included dental X-ray alignment systems, such as disclosed in U.S. Pat. No. 4,012,638—Altschuler et al. The latter patent discloses system for aligning a dental X-ray film relative to an X-ray beam, the system utilizing a plurality of infrared emitters and detectors positioned circumferentially about the path of the X-ray beam. A reflecting surface, having a plane parallel to the plane of the X-ray film holder and integral therewith, can be positioned parallel to the plurality of emitters and sensors by repositioning until the sensors receive a predetermined reflective response. Each sensor activates an indicator light seen on a display, and, when all the lights in a bank of lights are activated, alignment is indicated as being achieved.

Despite the obvious advantages of the above-described prior art systems and techniques, significant disadvantages or drawbacks still exist. For example, arrangements such as described above do not provide a digital dental system or method for real-time display of a patient's dental image to detect changes with respect to previous dental image(s) of the patient. Moreover, even if such systems are provided with redundancy, so that duplicate processors and display devices are utilized in order to provide dual images, such systems are not capable of providing the real-time display of the patient's dental image in an efficient manner, that is, in a very short timeframe.

Moreover, dental X-ray alignment systems, such as described above, are also characterized by certain disadvantages. Such systems place a substantial amount of reliance on the operation of the sensor or sensors utilized. That is to say, in such systems, the system operator or dentist is removed from the alignment procedure, and is replaced by electrical sensors, or the like. In this way, such systems provide the operator or dentist with no way of visually aligning the X-ray tube and the film or image intensifier (as the case may be).

SUMMARY OF INVENTION

According to the present invention, there is provided a digital dental system and method for real-time display of a patient's dental image to detect changes with respect to at least one previous dental image of the patient.

Specifically, such a digital dental system comprises an imaging unit for obtaining a dental image from the patient in real time and providing the dental image as electrical signals, a converter for converting the electrical signals to digital form, an input device for inputting further digital signals corresponding to the at least one previous dental image of the patient, a processor for processing the digital signals and the further digital signals to develop corresponding display signals and further display signals, and a plurality of display units (one for each of the digital signals and further digital signals) responsive to the display signals and the further display signals, respectively, for simultaneously and in real time displaying the dental image and the at least one previous dental image, respectively, of the patient.

The imaging unit of the system preferably comprises an X-ray tube for generating X-rays directed toward the teeth of the patient, an image intensifier for detecting the X-rays which pass through the teeth of the patient, and a television camera (or similar device) which scans the image intensifier to obtain the dental image from the patient in real time, so as to provide the dental image as electrical signals.

The processor of the digital dental system is, preferably, a whole picture processor which analyzes the dental image(s) in a rapid and economical manner. More specifically, the processor preferably comprises a video crossbar switch for receiving and routing the digital data corresponding to the image data from the X-ray tube, a plurality of memories (one for each display unit) for storing digital data corresponding to image data (either current or previous), various input/output devices (one for each memory) for providing data from the memory to the corresponding display unit for display, and a video processor for processing previous image data (as provided by a conventional peripheral unit, for example, a floppy disk). As seen below, the video crossbar switch functions to return data (read from the memory to the display unit) to the corresponding memory, as well as to route data to and from the video processor and its corresponding peripheral unit(s).

A preferred embodiment of the system further comprises an alignment device connected to the image intensifier and responsive to operator input for moving the image intensifier relative to the X-ray tube so as to maintain alignment therebetween. Such alignment procedure is very convenient for the operator or dentist to perform, and is also a much more definite system of alignment, since the operator or dentist can continue to align the image intensifier and X-ray tube until perfect alignment is visibly indicated on one of the display units.

The method of the present invention comprises a method for real-time display of a patient's dental image and at least one prior dental image of the patient on a display unit and at least one further display unit, respectively, the method comprising the steps of obtaining the dental image so as to provide corresponding electrical signals, converting the electrical signals to digital form, inputting further digital signals corresponding to the at least one previous dental image of the patient, processing the digital signals and the further digital signals to develop corresponding display signals and further display signals, and simultaneously and in real time displaying the dental image and the at least one previous dental image, respectively, of the patient.

The above-described digital dental system and method overcome many of the disadvantages which characterize systems and methods of the prior art. The conversion of the X-ray data to digital form, followed by storage on conventional peripheral units associated with the processor of the system, precludes the necessity for the X-rays to be stored manually in the dental files of the clinic or dentist; thus, possible loss or misplacement of the X-ray becomes less probable. In addition, immediate (real-time) display of the X-ray on one of the display units saves a significant amount of time for the dentist and the patient, since developing of the X-ray is no longer necessary. A further savings in time is experienced by the dentist and the patient, since the patient's previous X-rays are immediately available (in real time) and can be readily retrieved from the peripheral unit by the processor for immediate display; thus, it is unnecessary for previous X-rays to be located in, and retrieved from, manual files each time the patient visits the dentist or dental clinic. Moreover, after treatment is completed, it is unnecessary to replace the X-rays in the files, since the previous X-rays remain on the peripheral unit storage medium (for example, the patient's floppy disk). Finally, the possibility of error or oversight by the dentist in making a human/visual judgment in determining whether changes in the dental condition of a patient have taken place since the last visit is reduced considerably, or even eliminated, since the processor of the system may be utilized to analyze both past and current X-ray data (in accordance with conventional image processing techniques) to determine those changes which have taken place since the patient last visited the dentist or dental clinic.

Therefore, it is an object of the present invention to provide a system and method for real-time display of a patient's dental image to detect changes with respect to at least one previous dental image of the patient.

It is an additional object of the present invention to provide a system and method which employ digital storage of image information so as to preclude the necessity of providing manual storage facilities and techniques.

It is an additional object of the present invention to provide a system and method which employ digital processing, and preferably whole picture processing, of digital signals and further digital signals, corresponding to present and previous dental images, respectively, so as to preclude the necessity for time-consuming X-ray developing procedures and manual comparison/analysis of X-rays during each visit by the patient.

It is an additional object of the present invention to provide a system and method wherein proper alignment between the imaging unit and the patient can be achieved easily by the operator or dentist.

The above and other objects that will hereinafter appear, and the nature of the invention, will be more clearly understood by reference to the following description, the appended claims, and the accompanying drawings.

DETAILED DESCRIPTION

The invention of the application will now be more fully described with reference to FIG. 1, which is a diagrammatic representation of the digital dental system of the present invention.

Figure 1:
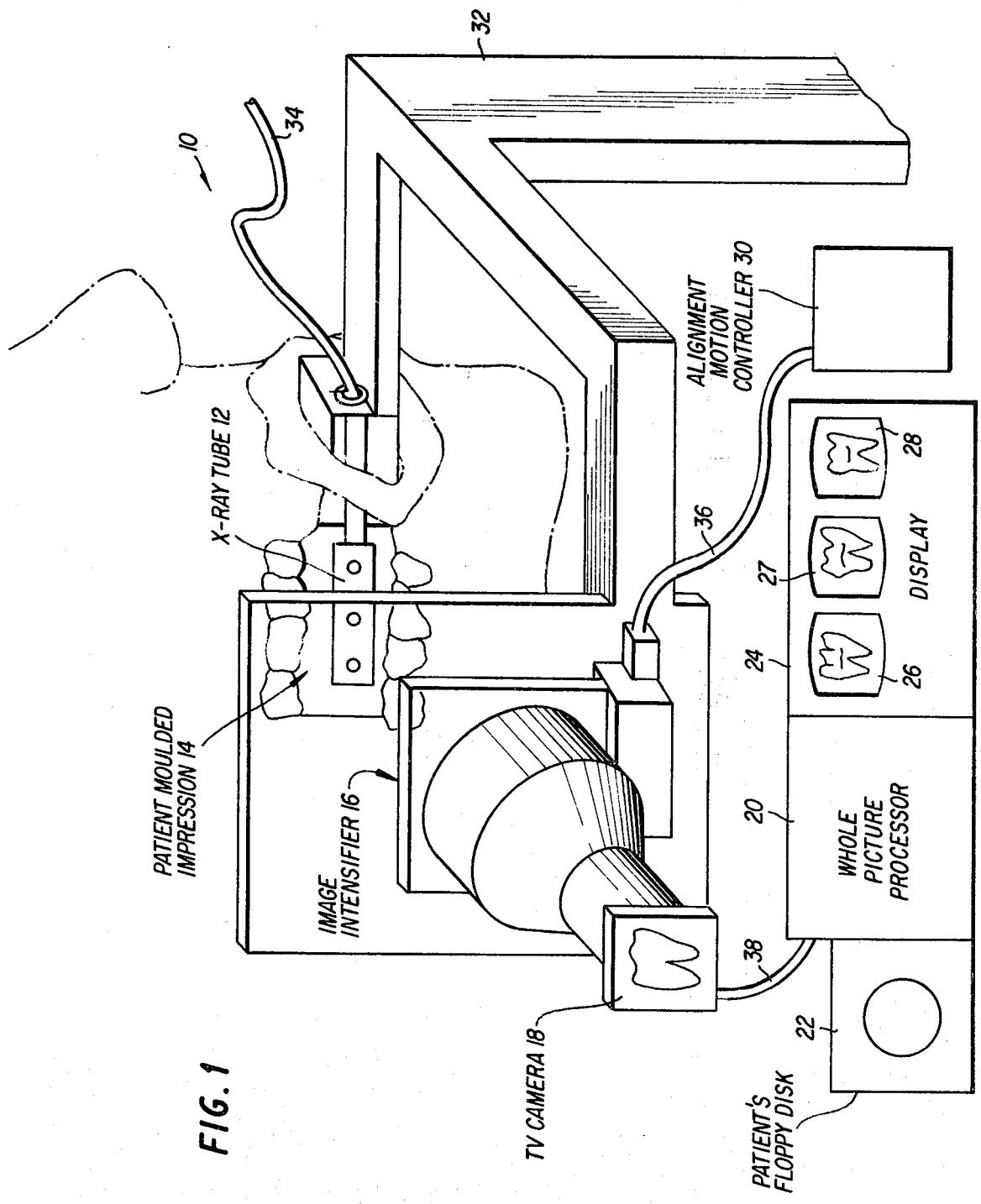
FIG. 1 is a diagrammatic representation of the digital dental system of the present invention.

As seen in FIG. 1, the digital dental system 10 comprises an X-ray tube 12 provided in a patient moulded impression 14, an image intensifier 16, a T.V. camera 18, a whole picture processor 20, a floppy disk 22, a display system 24 including multiple display units 26, 27 and 28, and an alignment motion controller 30.

As further seen in FIG. 1, the X-ray tube 12 and image intensifier 16 are mutually supported by a support member 32, the X-ray tube 12 is connected to an energizing source (not shown) by the lead 34, and the image intensifier 16 is connected to the alignment motion controller 30 via the lead 36. In addition, the T.V. camera 18 is connected to the whole picture processor 20 by lead 38.

In operation, when the patient visits the dentist or dental clinic, and X-rays are necessary, the X-ray tube 12 (which is contained within a patient moulded impression 14 which has been previously fabricated by known techniques) is inserted into the mouth of the patient. At the same time, an image intensifier 6 (which may be a fluorescent screen or other known device for intensifying the X-ray image) is placed at an appropriate point along the side of the cheek of the patient. The X-ray tube 12 is energized by an energization source (not shown) connected to X-ray tube 12 via lead 34. A support 32 may be provided in order to maintain a general positional relationship between the X-ray tube 12 and the image intensifier 16. As will be explained below, the image intensifier 16 is connected, via a lead 36, to an alignment motion controller 30 (which may be any known alignment device, such as that disclosed in previously discussed U.S. Pat. No. 4,012,638—Altschuler et al.). As indicated above, the operator or dentist utilizes the alignment motion controller 30 to obtain a precise alignment between the image intensifier 16 and the X-ray tube 12, such precise alignment being achieved by the operator or dentist as a result of visually checking the X-ray image on one of the display units 26-28.

Once the image intensifier 16 is properly aligned with the X-ray tube 12, the image or X-ray appearing on the image intensifier 16 continues to be scanned by the T.V. camera 18. T.V. camera 18 provides analog video signals via lead 38 to the whole picture processor 20.

The whole picture processor 20 operates, in a manner which will be described in more detail below with respect to FIG. 2, to display the current X-ray on one of the display units 26-28 (preferably, the first display unit 26).

In addition, at some point during the procedure, previous X-ray information relating to the patient can be read into the system from the patient's floppy disk 22 by the whole picture processor 20, and such previous X-ray information can be displayed on one or both of the remaining display units (preferably, display units 27 and 28).

In this manner, the dentist can, in real time, view both the current X-ray of the patient's teeth and the previous X-ray information relating to the patient, and can visually determine whether or not changes have taken place in the dental condition of the patient since the last visit.

However, a further significant advantage resides in the fact that the system and method of the present invention envision the employment of a whole picture processor 20 which, by conventional image processing techniques, can whole picture process each of the displayed images in real time, and can locate and identify differences between the respective images. Such image processing techniques are considered obvious to those of skill in the art, and are, for example, discussed in some detail in U.S. Pat. No. 4,229,797—Ledley.

Figure 2:
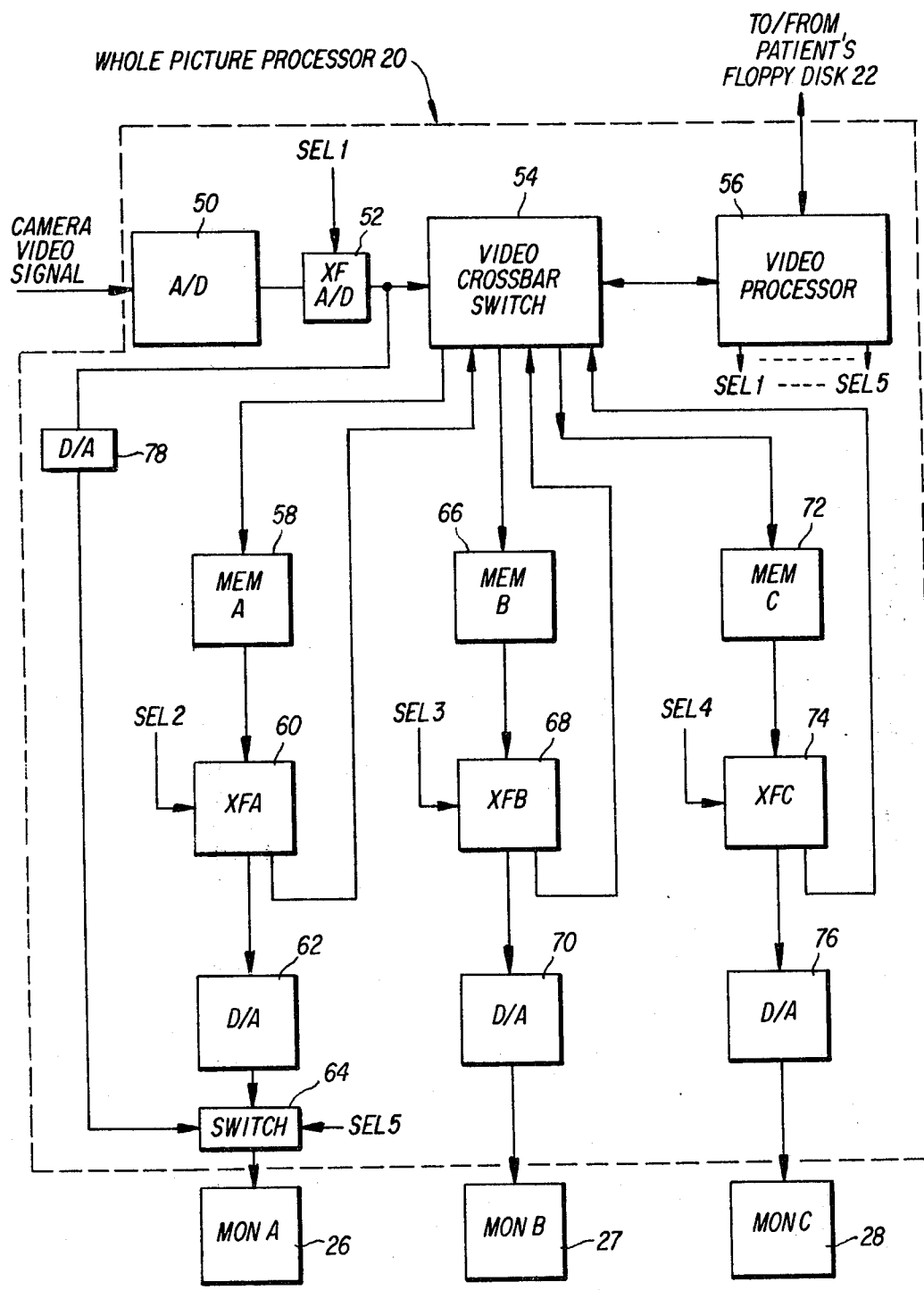
FIG. 2 is a block diagram of the whole picture processor of the system of the present invention.

FIG. 2 is a block diagram of the whole picture processor 20 of FIG. 1. As seen therein, the whole picture processor 20 comprises an analog-to-digital converter (ADC) 50, transfer unit 52, video crossbar switch 54, video processor 56, memories 58, 66 and 72, transfer units 60, 68 and 74, digital-to-analog converters (DAC) 62, 70 and 76, monitor switch 64, and further DAC 78.

In operation, the T.V. camera 18 (FIG. 1) operates in synchronization with the whole picture processor 20 (such synchronization being known to those of skill in the art) to scan the image intensifier 16, and to relay the resulting video signals to the whole picture processor 20. The ADC 50 (FIG. 2) in whole picture processor 20 receives the camera video signal and converts it to digital form. The resulting digital output is provided, via transfer gate 52, both to the video crossbar switch 54 and (via DAC 78 and switch 64) to display unit 26 (monitor A). This provides the system with the capability of operator monitoring of the image or picture being scanned by the video camera 18. The control signal SEL 1 is generated (via conventional operator control means) by video processor 56 in response to operator input, and provides for selective routing of the digital X-ray data either to the video crossbar switch 54 alone, or to the video crossbar switch 54 and display unit 26.

Digital data corresponding to current X-ray information received by the video crossbar switch 54 from transfer gate 52 is stored in memory 58. Previous X-ray information, contained on the patient's floppy disk 22, can be read into the video processor 56 by conventional means, and then provided via the video crossbar switch 54 to one or both of the memories 66 and 72. Thus, it should be recognized that the digital video crossbar switch 54, as the name implies, operates as a selector or router of signals from either the video camera 18 (FIG. 1) or the video processor 56 to the memories 58, 66 and 72.

Each memory 58, 66 and 72 is provided, at its output, with a corresponding transfer gate 60, 68 and 74, these transfer gates being enabled by control signals SEL 2, SEL 3 and SEL 4, respectively, provided by the video processor 56 in response to operator input controls (conventionally provided). As a result of enablement, transfer gates 60, 68 and 74 will provide previously stored information from memories 58, 66 and 72, respectively, to the video crossbar switch 54 for further provision to the video processor 56 if the video processor 56 is to be utilized for image analysis of the information. In addition, the transfer gates 60, 68 and 74, when properly enabled, will provide the stored information from memories 58, 66 and 72 (via DAC's 62, 70 and 76, respectively) to the display units 26, 27 and 28, respectively. In this manner, operator-controlled display of current or previous X-ray information as stored in respective memories can be provided on corresponding display units.

A transfer switch 64, having an output connected to display unit 26, has one of its inputs connected to DAC 62 and the other input connected to DAC 78. Thus, in accordance with the control signal SEL 5 issued by video processor 56 in response to operator input, switch 64 can be controlled to display, on display unit 26, either the current camera video signal (provided via ADC 50, transfer gate 52 and DAC 78) or the previously stored camera video signal (previously stored in memory 58 and provided via transfer gate 60 and DAC 62).

It should be recognized that memories 58, 66 and 72 can be any conventional high-speed refresh memory units. For example, each memory unit 58, 66 and 72 could be a CCD (charge-coupled device) memory with self-refreshing capability. As is well known in the art, such picture memories can be provided with timing control units for continuously circulating stored information synchronously at high (T.V. scan) rates with appropriate intervals for horizontal and vertical retrace, just as in a T.V. camera or monitor. This facilitates use of the memories 58, 66 and 72 as drivers for the monitors or display units 26-28.

The video crossbar switch 54 is a conventional unit which generally includes a collection of bus selectors and line selectors/deselectors (multiplexer/demultiplexer). The video crossbar switch performs the functions, inter alia, of source memory selection and designation memory selection (with reference to the memories 58, 66 and 72), as well as the routing of various inputs and outputs to and from, respectively, the video processor 56. Since the video crossbar switch 54 is a conventional piece of hardware, such as (for example) disclosed in U.S. Pat. No. 4,229,797—Ledley, it is not necessary for the video crossbar switch 54 to be shown or discussed, as to its operation, in further detail.

While preferred forms and arrangements have been shown in illustrating the invention, it is to be clearly understood that various changes in detail and arrangement may be made without departing from the spirit and scope of this disclosure.

What is claimed is:

1. A digital dental system for real time display of a patient's dental image to detect changes with respect to at least one previous dental image of the patient, comprising:

imaging means for obtaining a dental image from the patient in real time and providing said dental image as electrical signals;

converting means for converting said electrical signals to digital signals;

input means for inputting further digital signals corresponding to said at least one previous dental image of the patient;

processing means for processing said digital signals and said further digital signals to develop corresponding display signals and further display signals; and display means comprising a display unit and at least one further display unit responsive to said display signals and said further display signals, respectively, for simultaneously and in real time displaying said dental image and said at least one previous dental image, respectively of said patient wherein said processing means comprises a plurality of memories, one for each said display unit and said at least one further display unit, and a video crossbar switch connecting said converting means to said plurality of memories, said plurality of memories storing said digital signals and said further digital signals, respectively, said processing means further comprises a video processor connected to said video crossbar switch, said video crossbar switch being actuable for routing digital signals from said plurality of memories to said video processor, said video processor operating to whole picture process said digital signals to determine changes in the patient's dental image with respect to the at least one previous dental image of the patient.

2. The system of claim 1, wherein said imaging means comprises:

an X-ray tube for generating X-rays which are directed toward the teeth of the patient;

an image intensifier for detecting said X-rays which pass through the teeth of the patient; and a television camera which scans the image intensifier to obtain the dental image from the patient in real time, whereby to provide the dental image as electrical signals.

3. The system of claim 2, further comprising alignment means connected to said image intensifier and responsive to operator input for moving said image intensifier relative to said X-ray tube so as to maintain alignment therebetween.

4. The system of claim 1, wherein said input means comprises a disk unit.

5. The system of claim 1, wherein said at least one further display unit comprises one display unit.

6. The system of claim 1, wherein said at least one further display unit comprises two display units.

7. The system of claim 1, further comprising means connecting each of said plurality of memories to a corresponding one of said display unit and said at least one further display unit so as to provide said digital signals and said further digital signals for display on said plurality of display units, respectively.

8. The system of claim 7, further comprising additional converting means connected to said converting means for reconverting said digital signals to analog form, said connecting means comprising further converters, one for each of said plurality of memories, for converting said digital signals from said plurality of memories to analog form, and a switch connecting said additional converting means and a given one of said further converters, on the one hand, to said display unit, on the other hand, so as to selectively provide either a current dental image of the patient or a previously stored dental image of the patient to said display unit for display.

* * * * *